United States Patent

Ozark et al.

[11] Patent Number: 5,959,117
[45] Date of Patent: *Sep. 28, 1999

[54] MONOMERS USEFUL FOR CONTACT LENS MATERIALS

[76] Inventors: Richard M. Ozark, 626 Third St., Solvay, N.Y. 13209; Jay F. Kunzler, 6020 Monks Rd., Canandaigua, N.Y. 14424

[*] Notice: This patent is subject to a terminal disclaimer.

[21] Appl. No.: 09/131,756

[22] Filed: Aug. 10, 1998

[51] Int. Cl.$^6$ .......................... C07D 231/04; C07F 30/08
[52] U.S. Cl. .......................... 548/110; 526/279; 556/12; 523/107
[58] Field of Search .............................. 526/279; 548/110

[56] References Cited

U.S. PATENT DOCUMENTS

| | | | |
|---|---|---|---|
| 5,710,302 | 1/1998 | Kunzler et al. | 556/434 |
| 5,714,557 | 2/1998 | Kunzler et al. | 526/279 |

FOREIGN PATENT DOCUMENTS

| | | | |
|---|---|---|---|
| 9-221530 | 8/1997 | Japan | C08F 299/08 |

*Primary Examiner*—Johann Richter
*Assistant Examiner*—Dominic Keating
*Attorney, Agent, or Firm*—John E. Thomas; Denis A. Polyn

[57] ABSTRACT

Monomers of the following formula are useful in contact lens materials:

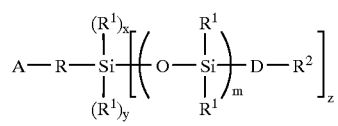

wherein:
A is an activated unsaturated group;
R and D independently are alkylene or haloalkylene radicals having 1 to 10 carbon atoms wherein said carbon atoms may include ether linkages therebetween;
each $R^1$ is independently selected from: alkyl or haloalkyl radical having 1 to 10 carbon atoms wherein ether linkages may be included between carbon atoms; siloxane groups; and carbocyclic ring groups having from 6 to 18 carbon atoms;
$R^2$ is selected from:

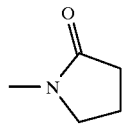

and

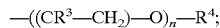

wherein $R^3$ is hydrogen or alkyl having 1–3 carbon atoms, n is 1 to 20; and $R^4$ is alkyl or haloalkyl radical having 1 to 10 carbon atoms wherein ether linkages may be included between carbon atoms;
m is an integer from 1 to 500; x and y are 0 or 1;
z is 1 or 2; and x+y+z=3.

24 Claims, No Drawings

MONOMERS USEFUL FOR CONTACT LENS MATERIALS

BACKGROUND OF THE INVENTION

The present invention relates to a class of silicone-containing monomers and their use in contact lens materials, especially silicone-containing contact lens materials. The monomers are especially useful in reducing modulus of silicone-containing contact lens materials.

Hydrogels represent a desirable class of materials for many biomedical applications including contact lenses. Hydrogels are hydrated, cross-linked polymeric system that contain water in an equilibrium state. Silicone hydrogels are a well known class of hydrogels and are characterized by the inclusion of a silicone-containing material. Silicone-containing monomers may be copolymerized with a wide variety of hydrophilic monomers to produce a variety of silicone hydrogel products. Either the silicone-containing monomer or the hydrophilic monomer may function as a crosslinking agent (a crosslinker being defined as a monomer having multiple polymerizable functionalities) or a separate crosslinker may be employed.

Many silicone hydrogels possess relatively high modulus (Young's modulus of elasticity). For many biomedical applications, including contact lens applications, it is desirable to provide hydrogels having reduced modulus, e.g. in the range of about 20 g/mm² to about 150 g/mm², and more preferably from about 30 g/mm² to about 100 g/mm². This is particularly important in the formation of soft contact lenses, as the modulus of the lens material can have a significant impact upon lens "comfort." Lenses possessing high modulus often have a perceived stiffness which may result in an unnatural feeling when worn upon the eye.

Another class of silicone materials useful for contact lens applications are non-hydrogels (referred to herein as "low water" materials). Low water silicone materials, like their hydrogel counterparts, are a copolymer of a silicone-containing monomer, however, unlike silicone hydrogels, "low water" silicone materials do not include appreciable amounts of hydrophilic monomers and/or internal wetting agents (i.e. typically less than 5 weight percent). As such, low water silicone materials, as their name suggest, do not absorb or retain appreciable amounts of water, e.g. less than about 5 weight percent, and more typically less than about 1 or 2 weight percent.

Although low water silicone compositions have very desirable oxygen permeability, they typically possess relatively high modulus (Young's modulus of elasticity). As for hydrogel contact lenses, the modulus of the lens material can have a significant impact upon lens "comfort."

U.S. Pat. Nos. 5,710,302 and 5,714,557 describe a class of silicone-containing monomers that are useful for reducing the modulus of silicone hydrogel or low water polymeric silicone compositions. The present invention provides additional silicone-containing monomers useful for reducing the modulus of such materials.

SUMMARY OF THE INVENTION

The present invention provides monomers of Formula I:

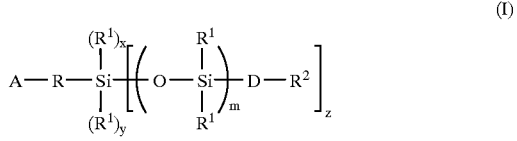

wherein:
A is an activated unsaturated group;
R and D independently are alkylene or haloalkylene radicals having 1 to 10 carbon atoms wherein said carbon atoms may include ether linkages therebetween;
each $R^1$ is independently selected from: alkyl or haloalkyl radical having 1 to 10 carbon atoms wherein ether linkages may be included between carbon atoms; siloxane groups; and carbocyclic ring groups having from 6 to 18 carbon atoms;
$R^2$ is selected from:

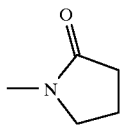

and

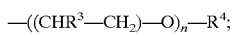

$-((CHR^3-CH_2)-O)_n-R^4;$ wherein $R^3$ is hydrogen or alkyl having 1–3 carbon atoms, n is 1 to 20; and $R^4$ is alkyl or haloalkyl radical having 1 to 10 carbon atoms wherein ether linkages may be included between carbon atoms;
m is an integer from 1 to 500; x and y are 0 or 1;
z is 1 or 2; and x+y+z=3.

The present invention further includes hydrogel and low-water silicone-containing compositions including the subject monomers, and contact lenses made from such compositions. A particular advantage of the subject monomers is that they are effective at reducing the modulus of such compositions without significantly reducing the oxygen permeability of the resultant polymeric composition.

DETAILED DESCRIPTION OF THE INVENTION

The present invention relates to monomers represented by Formula I (described below), and the use of such monomers to reduce the modulus of contact lens materials.

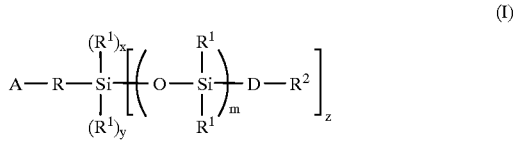

wherein:
A is an activated unsaturated group;
R and D independently are alkylene or haloalkylene radicals having 1 to 10 carbon atoms wherein said carbon atoms may include ether linkages therebetween;

each $R^1$ is independently selected from: alkyl or haloalkyl radical having 1 to 10 carbon atoms wherein ether linkages may be included between carbon atoms; siloxane groups; and carbocyclic ring groups having from 6 to 18 carbon atoms;

$R^5$ is selected from:

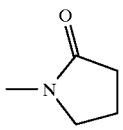

and

$-((CHR^3-CH_2)-O)_n-R^4;$ wherein $R^3$ is hydrogen or alkyl having 1–3 carbon atoms, n is 1 to 20; and $R^4$ is alkyl or haloalkyl radical having 1 to 10 carbon atoms wherein ether linkages may be included between carbon atoms;

m is an integer from 1 to 500; x and y are 0 or 1;

z is 1 or 2; and x+y+z=3.

Monomers of Formula I can be synthesized by general techniques known in the art. Specific representative methods are provided within the Examples.

With respect to A, the term "activated" is used to describe unsaturated groups which include at least one substituent which facilitates free radical polymerization, preferably an ethylenically unsaturated radical. This includes esters or amides of an acrylic or methacrylic acid represented by the general formula:

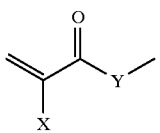

wherein X is preferably hydrogen or methyl but may include other groups, e.g. cyano, and Y represents —O—, —S—, or —NH—, but is preferably —O—. Examples of other suitable activated unsaturated groups include vinyl carbonates, vinyl carbamates, fumarates, fumaramides, maleates, acrylonitryl, vinyl ether and styryl.

Preferred compounds of Formula (I) are those where z is 1, and $R^1$ through $R^4$ are independently selected from alkyl groups, especially alkyl groups having from 1 to 10 carbon atoms, and fluoro-substituted lower alkyl groups. Preferably, m is 1 to 10, most preferably 1 or 2.

Specific examples of preferred monomers are represented by the following formulae:

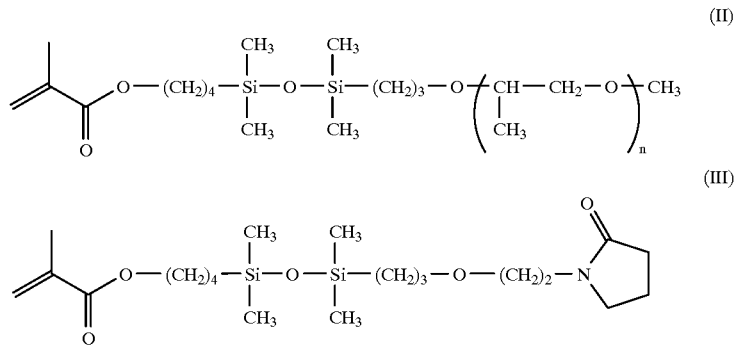

One class of contact lens materials for this invention is silicone hydrogels. A hydrogel is a crosslinked polymeric system that can absorb and retain water in an equilibrium state. Accordingly, silicone hydrogels are based on a silicone-containing monomer and a hydrophilic monomer. Silicone hydrogels of this invention are typically formed by polymerizing a monomer mixture comprising: about 1 to about 50 weight percent but preferably from about 5 to about 30 weight percent of monomers represented by Formula (I); about 10 to about 90 weight percent but preferably about 25 to about 50 weight percent of a silicone-containing monomer (in addition to the Formula (I) monomer); and about 10 to about 70 weight percent but preferably from about 20 to about 60 weight percent of a hydrophilic monomer.

Suitable hydrophilic monomers include: unsaturated carboxylic acids, such as methacrylic and acrylic acids; acrylic substituted alcohols, such as 2-hydroxyethylmethacrylate and 2-hydroxyethylacrylate; vinyl lactams, such as N-vinyl pyrrolidone; and acrylamides, such as methacrylamide and N,N-dimethylacrylamide.

One suitable class of silicone containing monomers include known bulky, monofunctional polysiloxanylalkyl monomers represented by Formula (IV):

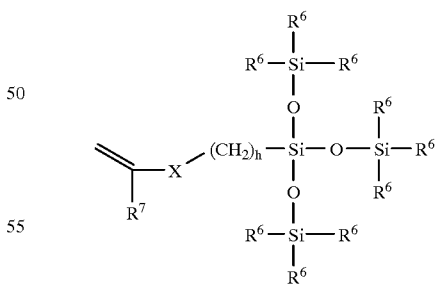

wherein:
X denotes —COO—, —CONR$^8$—, —OCOO—, or —OCONR$^8$— where each where $R^8$ is H or lower alkyl; $R^5$ denotes hydrogen or methyl; h is 1 to 10; and each $R^6$ independently denotes a lower alkyl or halogenated alkyl radical, a phenyl radical or a radical of the formula

$-Si(R^7)_3$ wherein each $R^7$ is independently a lower alkyl radical or a phenyl radical. Such bulky monomers specifically include methacryloxypropyl tris(trimethylsiloxy)silane, pentamethyldisiloxanyl methylmethacrylate, methyldi(trimethylsiloxy)methacryloxymethyl silane, 3-[tris(trimethylsiloxy)silyl] propyl vinyl carbamate, and 3-[tris(trimethylsiloxy)silyl] propyl vinyl carbonate.

Another suitable class are multifunctional ethylenically "end-capped" siloxane-containing monomers, especially difunctional monomers represented Formula (V):

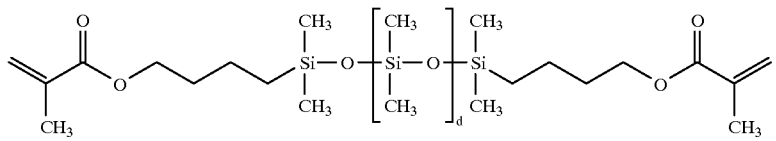

(Va)

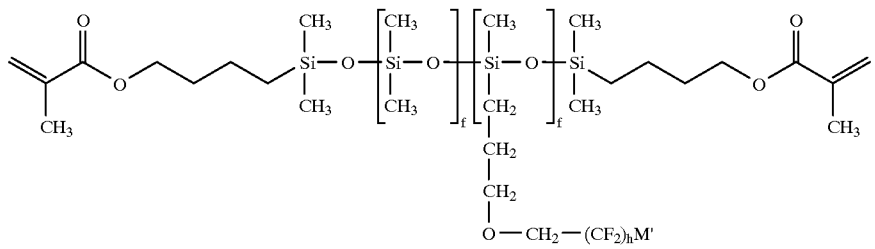

(Vb)

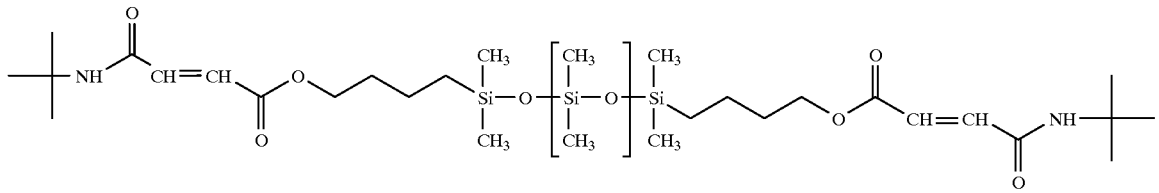

(Vc)

wherein:

d, f, g, h and k range from 0 to 250, preferably from 2 to 100; and

M' is hydrogen or fluorine.

Other silicone-containing monomers include the silicone-containing monomers described in U.S. Pat. Nos. 5,034,461, 5,610,252 and 5,496,871, the disclosures of which are incorporated herein by reference. Other silicone-containing monomers are well-known in the art.

In the case of silicone hydrogels, either the silicone-containing monomer or the hydrophilic monomer may function as a crosslinking agent (a crosslinker being defined as a monomer having multiple polymerizable functionalities) or a separate crosslinker may be employed. Examples of suitable crosslinking agents include: polyvinyl, typically di- or tri-vinyl monomers, most commonly the di- or tri(meth)acrylates of dihydric ethylene glycol, triethylene glycol, butylene glycol, hexane-1,6-diol and neopentyl glycol (such as ethylene glycol dimethacrylate, tetraethylene glycol dimethacrylate, and neopentyl glycol dimethacrylate); diallyl compounds like diallyl phthalate; divinylbenzene; and crosslinking agent having both a vinyl and a (meth)acrylic polymerizable group, such as the crosslinkers disclosed in U.S. Pat. No. 5,310,779.

Particularly preferred hydrogel compositions comprise from about 5 to about 20 weight percent of monomers represented by Formula (I), from 5 to 60 weight percent of

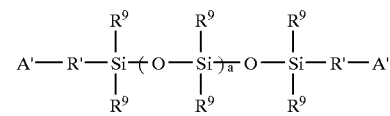

wherein:

each A' is independently an activated unsaturated group, similar to those radicals described for A in Formula (I);

each R' is independently an alkylene group having 1 to 10 carbon atoms wherein the carbon atoms may include ether, urethane or ureido linkages therebetween;

each $R^9$ is independently selected from monovalent hydrocarbon radicals or halogen substituted monovalent hydrocarbon radicals having 1 to 18 carbon atoms which may include ether linkages therebetween, and a is an integer equal to or greater than 1. Preferably, each $R^9$ is independently selected from alkyl groups, phenyl groups and fluoro-substituted alkyl groups. It is further noted that at least one $R^8$ may be a fluoro-substituted alkyl group such as that represented by the formula:

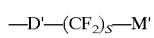

wherein:

D' is an alkylene group having 1 to 10 carbon atoms wherein said carbon atoms may include ether linkages therebetween;

M' is hydrogen, fluorine, or alkyl group but preferably hydrogen; and s is an integer from 1 to 20, preferably 1 to 6.

Specific examples of monomers of Formula (V) include the following:

the monomers represented by Formula (IV) or (V), from 20 to 60 weight percent of hydrophilic monomers, and from 0 to 10 weight percent of a crosslinking agent.

The monomer mixes employed in this invention, can be readily cured to cast shapes by conventional methods such as UV polymerization, or thermal polymerization, or combinations thereof, as commonly used in polymerizing ethylenically unsaturated compounds. In addition to the polymerization initiators, the monomer mixture may include colorants, or UV-absorbing agents known in the contact lens art.

When used in the formation of contact lenses, it is preferred that the subject hydrogels have water contents of from about 5 to about 70 weight percent. Furthermore, it is preferred that such hydrogels have a modulus from about 20 $g/mm^2$ to about 150 $g/mm^2$, and more preferably from about 30 $g/mm^2$ to about 100 $g/mm^2$.

Generally, the monomer mixtures is charged to a mold, and then subjected to light to effect curing of the monomer mixture in the mold. Various processes are known for curing a monomeric mixture in the production of contact lenses, including spincasting and static casting. Spincasting methods involve charging the monomer mixture to a mold, and spinning the mold in a controlled manner while exposing the monomer mixture to light. Static casting methods involve charging the monomer mixture between two mold sections, one mold section shaped to form the anterior lens surface and the other mold section shaped to form the posterior lens surface, and curing the monomer mixture by exposure to light. Such methods are described in U.S. Pat. Nos. 3,408,429, 3,660,545, 4,113,224, 4,197,266, and 5,271,875.

The low water silicone compositions of the present invention are formed by polymerizing a monomer mixture that includes no, or relatively minor amounts of, hydrophilic monomer, to ensure that the resultant copolymer does not absorb appreciable amounts of water. Preferred copolymers are prepared from monomer mixtures comprising: about 1 to about 50 weight percent, but preferably from 5 to 30 weight percent of monomers represented by Formula (I); and about 1 to about 99 weight percent, but more preferably from about 30 to about 60 weight percent of the silicone-containing monomer (in addition to the Formula (I) monomer), such as the monomers of Formulae (IV) or (V), above. When used in the formation of contact lenses, it is preferred that the subject low water silicone-containing copolymers hydrogels have water contents no more than 5 weight percent, and a modulus from about 20 $g/mm^2$ to about 150 $g/mm^2$, and more preferably from about 30 $g/mm^2$ to about 100 $g/mm^2$.

As an illustration of the present invention, several examples are provided below. These examples serve only to further illustrate aspects of the invention and should not be construed as limiting the invention.

EXAMPLE 1

Synthesis of pyrrolidinone-containing monomer of formula (III)—1-methacryloxypropyl)-3-(3-(oxyethylpyrrolidinone) propyl)tetramethyldisiloxane A. Synthesis of 1-(3-trimethylsiloxypropyl)-1-(hydrido) tetramethyldisiloxane.

To a 1 L-round bottom flask is added 1,3-tetramethyldisiloxane (100 g, 0.744 mole), allyloxytrimethylsilane (97.0 g, 0.745 mole), (tris(triphenylphosphine) rhodium) chloride (0.008 g, 8.8×10-6 mole) and 400 mL of anhydrous toluene. The solution is heated at 80° C. for 2 hours at which time the silicone hydride is reacted as shown by 1H NMR spectroscopy. The toluene is removed using a rotoevaporator and the resultant oil is vacuum distilled (65° C./1.5 mm Hg) to yield 127.5 g (64.8% yield) of trimethylsilyl protected hydroxypropyltetramethyldisiloxane. 1H NMR (CDCl3, TMS, (, ppm): 0.1 (s, 21H, Si—CH$_3$), 0.5 (t, 2H, Si—CH$_2$—), 1.65 (m, 2H, Si—CH$_2$—CH$_2$—CH$_2$), 3.45 (t, 2H, —CH$_2$—O), 4.6 (m, 1H, Si—H), High resolution GC MS, M=264, $C_{10}H_{28}O_2Si_3$.

B. Synthesis of 1-(3-Trimethylsilyloxypropyl)-3-(3-(oxyethylpyrrolidinone) propyl)tetramethydisiloxane.

To a 1 L-round bottom flask is added trimethylsilyl protected hydroxypropyltetramethyldisiloxane (30 g, 0.1135 mole), allyloxyethylpyrrolidinone (25 g, 0.147 mole), platinum divinyltetramethyldisiloxane complex (45 $\mu$l, 0.0025 mole/$\mu$l catalyst), 200 mL of THF and 200 mL of 1,4-dioxane. (The allyloxyethylpyrrolidinone is previously prepared by phase transfer catalyzed reaction of allylbromide with hydroxyethylpyrrolidinone). The solution is refluxed for 3 hours at which time the solvent is removed using a rotocvaporator. The resultant oil is passed through 50 g of silica gel using a 4/1 mixture of pentane and methylene chloride. The solvent is removed using a rotoevaporator and the resultant oil is vacuum distilled (160–170° C./0.05 mm Hg) to yield 33.2 grams (67.6% yield) of a 97% pure (by GC) 1-(3-trimethylsilyloxypropyl)-3-(3-(oxyethylpyrrolidinone)propyl)tetra-methyldisiloxane. 1H NMR and GC-MS confirmed structure.

C. Synthesis of 1-(3-Hydroxypropyl)-3-(3-(oxyethylpyrrolidinone) propyl)tetramethyldi-siloxane.

1-(3-trimethylsilyloxypropyl)-3-(3-(oxyethylpyrrolidinone)propyl)tetramethyldisiloxane (20 g, 0.0461 mole) is dissolved in 200 mL of methanol and to this solution is added 4.0 mL of 10% solution of acetic acid at room temperature. The mixture is stirred for 1 hr and the solvent is removed on a rotoevaporator at 40° C. resulting in a quantitative yield of 1-(3-hydroxypropyl)-3-(3-(oxyethylpyrrolidinone) propyl)tetramethyldisiloxane. The deprotected product is dissolved in 300 mL of chloroform and washed four times with distilled water. The organic layer is collected, dried over magnesium sulfate and filtered. 1H NMR and GC MS confirmed structure.

D. Synthesis of 1-(Methacryloxypropyl)-3-(3-oxyethylpyrrolidinone)propyl)tetramethyl-disiloxane.

The deprotected hydroxypropyltetramethyldisiloxane reaction product (16.7 g, 0.0461 mole) and triethylamine (5.36 g, 0.0530 mole) are added to a 1 L-round bottom flask. The solution is cooled to 0° C. and methacryloyl chloride (5.54 g, 0.0830 mole) is slowly added. Following the addition, the solution is brought to room temperature and allowed to stir overnight. The next day the resultant solution is extracted two times with 1N HCl, two times with 2 N NaOH and two times with distilled water. The organic layer is collected and dried over magnesium sulfate. The solution is filtered and the solvent is removed. The resultant oil is passed through 50 g of silica gel using a 10/1 mixture of pentane and methylene chloride. The solvent is removed using a rotoevaporator. The resultant oil is vacuum stripped at 60° C. (0.05 mm Hg) for one hour to yield 11 grams of a 92.9% pure (by GC) 1-(methacryloxypropyl)-3-(3-(oxyethylpyrrolidinone)propyl)-tetramethyldisiloxane. 1H NMR and GC MS confirmed structure.

EXAMPLE 2

Synthesis of 2-propyleneoxy-containing monomer of formula (II)—1-(methacryloxy)3-(3-(propyleneglycol monomethylether)propyl) tetramethyldisiloxane A. Synthesis of 1-(3-Trimethylsilyloxypropyl)-3-(3-(propyleneglycolmonomethylether)-propyl) tetramethyldisiloxane.

To a 1 L round bottom flask is added trimethylsilyl protected hydroxy propyl tetramethyldisiloxane (as prepared in Example 1) (30 g, 0.1135 mole), allyloxypropyleneglycolmethylether (27.7 g, 0.147 mole), platinum divinyltetramethyldisiloxane complex (45 ul, 0.0025 mole/ul catalyst), 100 mL of THF and 150 mL of 1,4-dioxane. (The allyloxypropyleneglycolmethylether is prepared previously by phase transfer catalyzed reaction of allylbromide with propylene glycol monomethylether.) The solution is refluxed for 3 hours at which time the solvent is removed using a rotoevaporator. The resultant oil is passed through 50g of silica gel using a 4/1 mixture of pentane and methylene chloride. The solvent is removed using a rotoevaporator and the resultant oil is vacuum distilled (140° C./0.1 mm Hg) to yield 42.2 grams (82.2% yield) of a 98.1% pure (by GC) 1-(3-trimethylsilyloxypropyl)-3-(3-(propyleneglycolmethylether)propyl)tetramethyldisiloxane. 1H NMR and GC-MS confirmed structure.

B. Synthesis of 1-(3-Hydroxypropyl)-3-(3-(propyleneglycolmethylether)propyl) tetramethyldisiloxane.

1-(3-trimethylsilyloxypropyl)-3-(3-(propyleneglycolmethyl-ether)propyl) tetramethyldisiloxane (42 g, 0.0442 mole) is dissolved in 420 mL of methanol and to this solution is added 7.5 mL of 10% solution of acetic acid at room temperature. The mixture is stirred for 1 hour and the solvent is removed on a rotoevaporator at 40° C. resulting in a quantitative yield of 1-(3-hydroxypropyl)-3-(3-(propyleneglycolmethylether)propyl) tetramethyldisiloxane. The deprotected product is dissolved in 300 mL of a 50/50 mixture of hexane and diethylether and washed four times with distilled water. The organic layer is collected, dried over magnesium sulfate and filtered. 1H NMR and GC MS confirmed structure.

C. Synthesis of 1-(Methacryloxypropyl)-3-(3-(propyleneglycolmethylether)propyl) tetramethyldisiloxane.

The deprotected hydroxypropyltetramethyldisiloxane reaction product (35.3 g, 0.0928 mole) and triethylamine (10.0 g, 0.097 mole) are added to a 1 L round bottom flask. The solution is cooled to 0° C. and methacryloyl chloride (10.1 g, 0.097 mole) is slowly added. Following the addition, the solution is brought to room temperature and allowed to stir overnight. The next day the resultant solution is extracted two times with 1 N HCl, two times with 2 N NaOH and two times with distilled water. The organic layer is collected and dried over magnesium sulfate. The solution is filtered and the solvent is removed. The resultant oil is passed through 50 g of silica gel using a 30% methylene chloride/70% pentane mixture. The solvent is removed using a rotoevaporator. The resultant oil is vacuum stripped at 60° C. (0.05 mm Hg) for one hour to yield 33 grams of a 96.2% pure (by GC) 1-(methacryloxypropyl)-3-(3-(propyleneglycolmethylether)-propyl) tetramethyldisiloxane. 1H NMR and GC MS confirmed structure.

EXAMPLES 3 to 5

A series of monomer mixtures, suitable for providing silicone hydrogel contact lenses, were prepared by mixing the following components: a compound of Example 1; 3-methacryloxypropyl tris(trimethylsiloxy)silane (TRIS); N,N-dimethylacrylamide (DMA); and ethyleneglycoldimethacrylalte (EGDMA) as a crosslinking agent. The amounts of each component mixture (based on weight) are listed in the following table, composition "Cl" designating a control composition containing no Formula (II) compound. Additionally, to each mixture was added Darocur-1173™ initiator (0.5 parts by weight (pbw)).

The monomer mixtures were cured into films by placing the mixture between two silane-treated glass plates and exposing to a light source for one hour. Cured films were released from the plates and extracted with isopropanol, then heated in boiling water for one hour. Films were equilibrated in borate buffered saline before characterization. Mechanical properties of the films were determined using ASTM methods 1708 and 1938; oxygen permeability was tested by a polarograhic probe method.

The results are summarized in the following table.

TABLE 1

| Example | Composition (Wt. %) Formula III/ TRIS/ DMA/EGDMA | Young's Modulus (g/mm$^2$) | Tear Strength (g/mm) | Dk | Percent Water |
| --- | --- | --- | --- | --- | --- |
| C1 | 0/70/30/0.5 | 236 | 67 | 106 | 20 |
| Ex 3 | 65/5/30/0.5 | 98 | 39 | 92 | 19 |
| Ex 4 | 60/10/30/0.5 | 56 | 25 | 78 | 20 |
| Ex 5 | 50/20/30/0.5 | 44 | 13 | 66 | 26 |

As seen in the Table, the formula (II) compound of the invention was useful in reducing modulus and providing materials with properties suitable for contact lens applications.

EXAMPLES 6 to 8

A series of monomer mixtures, suitable for providing silicone hydrogel contact lenses, were prepared by mixing the following components: a compound of Example 2; 3-methacryloxypropyl tris(trimethylsiloxy)silane (TRIS); N,N-dimethylacrylamide (DMA); and ethyleneglycoldimethacrylalte (EGDMA) as a crosslinking agent. The amounts of each component mixture (based on weight) are listed in the following table. Additionally, to each mixture was added Darocur-1173™ initiator (0.5 parts by weight (pbw)).

The monomer mixtures were cured into films and evaluated as in Example 3. The results are summarized in the following table.

TABLE 2

| Example | Composition (Wt. %) Formula III/ TRIS/ DMA/Xlinker | Young's Modulus (g/mm$^2$) | Tear Strength (g/mm) | Dk | Percent Water |
| --- | --- | --- | --- | --- | --- |
| C1 | 0/70/30/0.5 | 236 | 67 | 106 | 20 |
| Ex 6 | 65/5/30/0.5 | 66 | 40 | 100 | 18 |
| Ex 7 | 60/10/30/0.5 | 44 | 26 | 97 | 18 |
| Ex 8 | 50/20/30/0.5 | 29 | 15 | 79 | 18 |

The first composition was a control and included none of the monomer represented by Formula (II), which had a significantly higher modulus than the other compositions which included the Formula (II) monomer of the invention.

Many other modifications and variations of the present invention will be evident to a person of ordinary skill in the art, and it is understood that, within the scope of the claims, the present invention can be practiced other than as specifically described.

We claim:

1. A monomer represented by Formula I:

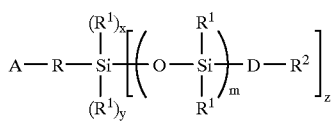

wherein:

A is an activated unsaturated group;

R and D independently are alkylene or haloalkylene groups having 1 to 10 carbon atoms wherein said carbon atoms may include ether linkages therebetween;

each $R^1$ is independently selected from: alkyl or haloalkyl groups having 1 to 10 carbon atoms wherein ether linkages may be included between carbon atoms; siloxane groups; and carbocyclic ring groups having from 6 to 18 carbon atoms;

$R^2$ is selected from:

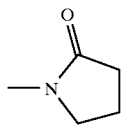

and

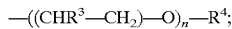

wherein $R^1$ is hydrogen or alkyl having 1–3 carbon atoms, n is 1 to 20; and $R^4$ is alkyl or haloalkyl groups having 1 to 10 carbon atoms wherein ether linkages may be included between carbon atoms;

m is an integer from 1 to 500; x and y are 0 or 1;

z is 1 or 2; and x+y+z=3.

2. The monomer of claim 1 wherein z is 1, and $R_1$ and $R_2$ are independently selected from alkyl groups having from 1 to 10 carbon atoms.

3. The monomer of claim 1 wherein A is a group selected from an ester or amide of acrylic acid or methacrylic acid.

4. The monomer of claim 1 wherein R and D are alkylene having from 1 to 6 carbon atoms wherein said carbon atoms may include ether linkages therebetween.

5. The monomer of claim 1 wherein $R_1$, $R_2$, $R_3$ and $R_4$ are independently selected from alkyl groups having from 1 to 10 carbon atoms.

6. The monomer of claim 1 wherein n is from 1 to 6; and m is from 1 to 10.

7. A monomer of claim 1 represented by Formula (II):

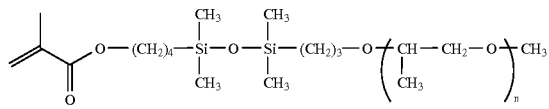

8. A monomer of claim 1 represented by Formula (III):

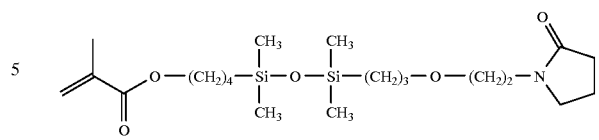

9. A composition formed by polymerizing a monomer mixture comprising a monomer represented by Formula I:

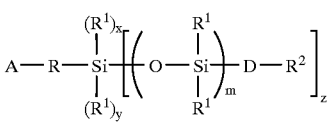

wherein:

A is an activated unsaturated group;

R and D independently are alkylene or haloalkylene groups having 1 to 10 carbon atoms wherein said carbon atoms may include ether linkages therebetween;

each $R^1$ is independently selected from: alkyl or haloalkyl group having 1 to 10 carbon atoms wherein ether linkages may be included between carbon atoms; siloxane groups; and carbocyclic ring groups having from 6 to 18 carbon atoms;

$R^2$ is selected from:

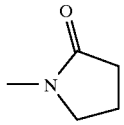

and

wherein $R^3$ is hydrogen or alkyl having 1–3 carbon atoms, n is 1 to 20; and $R^4$ is alkyl or haloalkyl group having 1 to 10 carbon atoms wherein ether linkages may be included between carbon atoms;

m is an integer from 1 to 500; x and y are 0 or 1;

z is 1 or 2; and x+y+z=3.

10. The composition of claim 9 wherein z is 1 and $R_1$, $R_2$, $R_3$ and $R_4$ are independently selected from alkyl groups having from 1 to 10 carbon atoms.

11. The composition of claim 9 wherein A is a group selected from an ester or amide of acrylic acid or methacrylic acid.

12. The composition of claim 9 wherein R and D are alkylene having from 1 to 6 carbon atoms wherein said carbon atoms may include ether linkages therebetween; n is from 1 to 6; and m is from 1 to 10.

13. The composition of claim 9 wherein the monomer mixture includes a monomer represented by Formula (II):

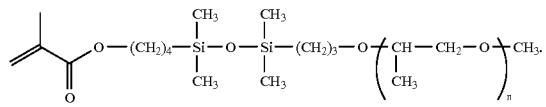

14. The composition of claim 9 wherein the monomer mixture includes a monomer represented by Formula (III):

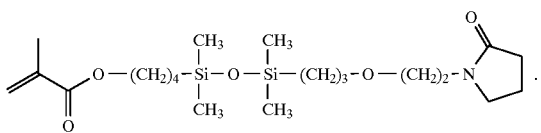

15. The composition of claim 9 formed by polymerizing a monomer mixture comprising a monomer of Formula (I), and a silicone-containing monomer other than a Formula (1) monomer.

16. The composition of claim 15 wherein the monomer mixture further comprises a hydrophilic monomer.

17. The composition of claim 15 wherein said silicone-containing monomer includes methacryloxypropyl tris(trimethylsiloxy)silane.

18. The composition of claim 9 wherein the monomer mixture further comprises a hydrophilic monomer.

19. The composition of claim 9, which is a hydrogel.

20. A contact lens formed of the polymerization product of the composition of claim 9.

21. A contact lens formed of the polymerization product of the composition of claim 13.

22. A contact lens formed of the polymerization product of the composition of claim 14.

23. A contact lens formed of the polymerization product of the composition of claim 15.

24. A contact lens formed of the polymerization product of the composition of claim 19.

* * * * *

UNITED STATES PATENT AND TRADEMARK OFFICE
CERTIFICATE OF CORRECTION

PATENT NO. : 5,959,117
DATED : Sep. 28, 1999
INVENTOR(S) : Richard M. Ozark, Jay F. Kunzler It is certified that error appears in the above-identified patent and that said Letters Patent is hereby corrected as shown below:

On the title page: Item [73]

-- Assignee: Bausch & Lomb Incorporated, Rochester, New York --, insert

Signed and Sealed this

Twenty-sixth Day of September, 2000

Attest:

Q. TODD DICKINSON

*Attesting Officer*  *Director of Patents and Trademarks*